(12) United States Patent
Ishihara et al.

(10) Patent No.: US 7,964,759 B2
(45) Date of Patent: Jun. 21, 2011

(54) METHOD FOR PRODUCING 3,3,3-TRIFLUOROPROPYNE

(75) Inventors: Akira Ishihara, Kawagoe (JP); Yasuo Hibino, Shiki (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/596,321

(22) PCT Filed: Apr. 4, 2008

(86) PCT No.: PCT/JP2008/056764
§ 371 (c)(1),
(2), (4) Date: Oct. 16, 2009

(87) PCT Pub. No.: WO2008/132964
PCT Pub. Date: Nov. 9, 2008

(65) Prior Publication Data
US 2010/0145112 A1 Jun. 10, 2010

(30) Foreign Application Priority Data

Apr. 17, 2007 (JP) ................................. 2007-108024
Apr. 3, 2008 (JP) ................................. 2008-096726

(51) Int. Cl.
*C07C 17/25* (2006.01)
(52) U.S. Cl. ........................................ 570/155; 570/156
(58) Field of Classification Search ........................ None
See application file for complete search history.

(56) References Cited

U.S. PATENT DOCUMENTS

2003/0060670 A1 * 3/2003 Nair et al. ..................... 570/155

FOREIGN PATENT DOCUMENTS

JP 6-279330 A 10/1994
JP 2005-504097 A 2/2005

OTHER PUBLICATIONS

Makosza et al, Tetrahedron, 2002, 58, 7295-7301.*
International Search Report with English translation dated Jun. 24, 2008 (Two (2) pages).
PCT/ISA/237 dated Jun. 24, 2008 (Two (2) pages).
Haszeldine, R. N., "The Reactions of Fluorocarbon Radicals. Part IV. The Synthesis of 3:3:3-Trifluoropropyne", J. Chem Soc., 1951, pp. 588-591.
Albert L. Henne, et al., "Trifluoropropyne", Journal of the American Chemical Society, 1951, vol. 73, pp. 1042-1043.
Haszeldine, R. N., "Reactions of Fluorocarbon Radicals. Part V. Alternative Syntheses for Trifluoromethylacetylene (3:3:3-Trifluoropropyne), and the Influence of Polyfluoro-groups on Adjacent Hydrogen and Halogen Atoms", Journal of the Chemical Society, 1951, pp. 2495-2504.
Haszeldine, R. N., "Reactions of Fluorocarbon Radicals. Part VI. The Hydration of Trifluoromethyl- and Pentafluorotheyl-substituted Acetylenes", Journal of the Chemical Society, 1952, pp. 3483-3490.
William G. Finnegan, et al., "Improved Synthesis of 3,3,3-Trifluoropropyne", Journal of Organic Chemistry, 1963, pp. 1139-1140, vol. 28.
J.J. Mielcarek, et al,, "A New Synthesis for Fluoroacetylenes. Potassium Fluoride as a Dehydro-iodination Agent", Journal of Fluorine Chemistry, 1978, pp. 321-324 vol. 12.
G.A. Olah, "Fluorination Reactions of Sulfur Tetrafluoride", Journal of the American Chemical Society, 1959, pp. 3165-3166, vol. 81.

* cited by examiner

*Primary Examiner* — Sudhakar Katakam
(74) *Attorney, Agent, or Firm* — Crowell & Moring LLP

(57) ABSTRACT

Disclosed is a method for producing 3,3,3-trifluoropropyne, which is characterized in that a base is reacted with (Z)-1-halogeno-3,3,3-trifluoropropene represented by formula [1]. It is possible by this production method to obtain 3,3,3-trifluoropropyne with high yield. Furthermore, since waste disposal is also easy, it is a production method that is industrially advantageous.

7 Claims, No Drawings

METHOD FOR PRODUCING 3,3,3-TRIFLUOROPROPYNE

TECHNICAL FIELD

The present invention relates to a method for producing 3,3,3-trifluoropropyne, which can become a functional material, such as refrigerant, etching agent, aerosol, etc., or physiologically active substance, an intermediate of functional materials, or a monomer of polymer compounds.

BACKGROUND OF THE INVENTION 3,3,3,-trifluoropropyne has a trifluoromethyl group and a triple bond in the molecule and has special properties. Therefore, there have been many studies of the use of simple substance and its derivatives.

As a method for producing 3,3,3-trifluoropropyne, for example, Non-patent Publications 1-3 disclose a method of obtaining it from 2,3-dibromo-1,1,1-trifluoropropene, and Non-patent Publication 4 discloses a method of deriving it from 1,1,2-trichloro-3,3,3-trifluoropropene.

Furthermore, Non-patent Publication 5 reports a method of reacting 1-iodo-3,3,3-trifluoropropene with potassium fluoride (KF), and Non-patent Publication 6 reports a method of reacting acetylenecarboxylic acid (HC≡CCOOH) with sulfur tetrafluoride ($SF_4$).

Non-patent Publication 1: Journal of the American Chemical Society, 1951, 73, 1042-3.
Non-patent Publication 2: Journal of the Chemical Society, 1951, 2495-504.
Non-patent Publication 3: Journal of the Chemical Society, 1952, 3483-90.
Non-patent Publication 4: Journal of Organic Chemistry, 1963, 28, 1139-40.
Non-patent Publication 5: Journal of Fluorine Chemistry, 1978, 12(4), 321-4.
Non-patent Publication 6: Journal of the American Chemical Society, 1959, 81, 3165-6.

SUMMARY OF THE INVENTION

The method described in Non-patent Publications 1-3 is, as shown in the following scheme, a method for producing 3,3,3-trifluoropropyne by using 3,3,3-trifluoropropene as the starting raw material.

(Scheme 1)

[Chemical Formula 1]

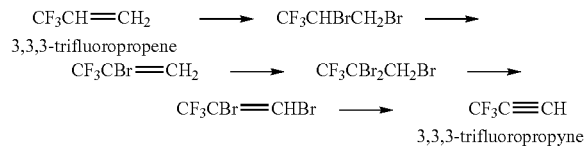

3,3,3-trifluoropropyne

This method, however, generally requires a multi-stage step. Therefore, it becomes complicated. Furthermore, since it uses bromine, which is heavily corrosive, it requires a reaction container that is resistant to corrosiveness. Therefore, its industrial use is difficult.

Furthermore, the method of Non-patent Publication 4 uses a zinc compound relative to 1,1,2-trichloro-3,3,3-trifluoropropene. Therefore, the disposal of zinc liquid waste becomes problematic.

Furthermore, in the method of Non-patent Publication 5, the raw material is expensive, by-products are produced much together with the target product, and the target product is in an extremely low yield (20%). Therefore, its use is difficult as an industrial method.

In the method of Non-patent Publication 6, acetylenecarboxylic acid as the raw material is expensive, and furthermore sulfur tetrafluoride, which is difficult in handling, is used. Therefore, it was not necessarily an industrial method.

As mentioned above, they are not necessarily satisfactory methods as industrial production methods used for mass-production of 3,3,3-trifluoropropyne, which is the target product of the present invention. Therefore, there has been a demand for establishing the production method that is easy to implement the target product in industrial scale.

As a result of a repeated eager study to solve the above task, the present inventors have found that 3,3,3-trifluoropropyne is obtained with high yield and high selectivity by reacting a base with (Z)-1-halogeno-3,3,3-trifluoropropene represented by formula [1]

[Chemical Formula 2]

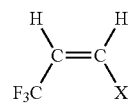

[1]

(In the formula, X represents a fluorine, chlorine, or bromine), thereby completing the present invention.

The present invention is characterized in using (Z)-1-halogeno-3,3,3-trifluoropropene. Since 1-halogeno-3,3,3-trifluoropropene has a double bond in the reaction system, there exist cis (Z) form and trans (E) form.

[Chemical Formula 3]

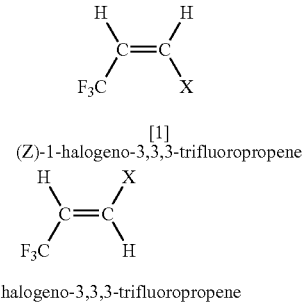

(Z)-1-halogeno-3,3,3-trifluoropropene (E)-1-halogeno-3,3,3-trifluoropropene

For example, in case that it is conducted similar to the present invention by using the trans form, that is, (E)-1-halogeno-3,3,3-trifluoropropene as the starting raw material, the reaction does not proceed at all (conversion: 0%), and the corresponding 3,3,3-trifluoropropyne is never obtained (see the after-mentioned Reference Example 1).

From this, the inventors had expected at the beginning that, even in the case of using the cis form, that is, (Z)-1-halogeno-3,3,3-trifluoropropene as the starting raw material, the reaction would not proceed similarly, and it would be difficult to efficiently produce 3,3,3-trifluoropropyne.

The present inventors, however, have obtained a practically advantageous finding, which is extremely easy as a production method in industrial scale, that 3,3,3-trifluoropropyne can be obtained with higher yield and higher selectivity as compared with conventional techniques, when using (Z)-1-halogeno-3,3,3-trifluoropropene as the starting raw material.

(Z)-1-halogeno-3,3,3-trifluoropropene has a trifluoromethyl group ($CF_3$). It is assumed that, due to a strong electron-attracting property of trifluoromethyl group, a compound having a trifluoromethyl group in the vicinity of a double bond is greatly different in reactivity from a substrate not having that, and a preferable effect was obtained when using (Z)-1-halogeno-3,3,3-trifluoropropene as the raw material.

Furthermore, as mentioned hereinafter in detail, the present inventors also have obtained a finding that the reaction proceeds sufficiently even under a condition that solvent is not made to coexist, that is, even by using only (Z)-1-halogeno-3,3,3-trifluoropropene and base.

In this way, the present invention makes it possible to produce the target compound in a reaction condition that is industrially operable and easy, with a higher yield than those of conventional techniques. Furthermore, the reaction proceeds well even in a condition that organic solvent is not made to coexist. Therefore, it does not put an environmental burden, and it has become possible to produce the target 3,3,3-trifluoropropyne with high productivity.

DETAILED DESCRIPTION

According to the present invention, it is possible to obtain 3,3,3-trifluoropropyne with high yield by reacting a base with (Z)-1-halogeno-3,3,3-trifluoropropene under a mild condition. Furthermore, even in the case of using solvent, recycle is possible by recovering the used solvent, too. Since waste disposal is also easy, it is possible to provide a production method that is industrially advantageous.

In the following, the present invention is explained in more detail. The present invention is a method for producing 3,3,3-trifluoropropyne, characterized in that a base is reacted with (Z)-1-halogeno-3,3,3-trifluoropropene represented by formula [1]. In the following, it is shown as Scheme 2.

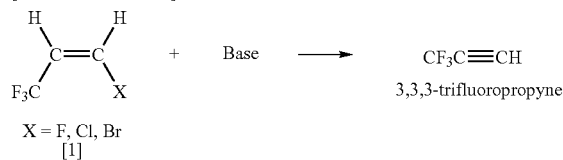

(Scheme 2)

[Chemical Formula 4]

X = F, Cl, Br
[1]

3,3,3-trifluoropropyne

As (Z)-1-halogeno-3,3,3-trifluoropropene represented by formula [1], which is the starting raw material of the present invention, specifically (Z)-1,3,3,3-tetrafluoropropene, (Z)-1-chloro-3,3,3-trifluoropropene, and (Z)-1-bromo-3,3,3-trifluoropropene are cited. Of these, due to availability, usefulness of the compound to be obtained, etc., (Z)-1-chloro-3,3,3-trifluoropropene and (Z)-1,3,3,3-tetrafluoropropene are preferably used.

Furthermore, of (Z)-1-halogeno-3,3,3-trifluoropropene to be used in the present invention, it is possible to obtain (Z)-1-chloro-3,3,3-trifluoropropene together with (E)-1-chloro-3,3,3-trifluoropropene by conducting a gas-phase fluorination reaction by chromium catalyst or a liquid-phase fluorination reaction with no catalyst to 1,1,1,3,3-pentachloropropane. Both isomers can easily be separated by distillation.

Furthermore, it is possible to obtain (Z)-1,3,3,3-tetrafluoropropene together with (E)-1,3,3,3-tetrafluoropropene by subjecting 1,1,1,3,3-pentafluoropropane to alkali decomposition. Both can be separated by distillation.

As the base used in the method of the present invention, it is possible to use organic bases such as alkylamines, pyridines, anilines, guanidines, lutidines, morpholines, piperidines, pyrrolidines, pyrimidines, pyridazines, etc., and inorganic bases such as ammonia, alkali metal alkoxide, alkali metal carbonate, alkali-earth metal carbonate, alkali metal carboxylate, alkali-earth metal carboxylate, alkali metal hydroxide, alkali-earth metal hydroxide, etc.

As specific examples of the organic base, it is possible to cite triethylamine, diethylamine, diethylaminopyridine, N,N-dimethylaniline, dimethylbenzylamine, guanidine, N,N-diethylaniline, 1,8-diazabicyclo[5,4,0]undecene-7,1,4-diazabicyclo[2,2,2]octane, pyridine, 2,4,6-trimethylpyridine, dimethylaminopyridine, 2,6-lutidine, 2-methylpyridine, N-methylmorpholine, piperidine, pyrrolidine, pyrimidine, pyridazine, and morpholine.

It is one of preferable modes to use a base having high basicity, for example, guanidine, 1,8-diazabicyclo[5,4,0]undecene-7, etc., of the organic bases, since the reaction time is shortened, too. Furthermore, "high basicity" mentioned herein refers to a base having a pH of 8 or higher, mainly one having a pH of 10 or higher.

Furthermore, the reaction proceeds even with triethylamine, diethylamine, dimethylaminopyridine, N,N-dimethylaniline, dimethylbenzylamine, N,N-diethylaniline, pyridine, 2,4,6-trimethylpyridine, dimethylaminopyridine, 2,6-lutidine, 2-methylpyridine, N-methylmorpholine, piperidine, pyrrolidine, pyrimidine, pyridazine, morpholine, etc., which are bases having midrange strengths. There is small merit to particularly use them, since they also require a further reaction time as compared with bases having high basicity.

Of the above-mentioned examples of inorganic base, an alkali metal hydroxide or alkali-earth metal hydroxide is preferable, due to economy and handling easiness. Furthermore, herein alkali metal refers to lithium, sodium, potassium, rubidium, or cesium, and alkali-earth metal refers to magnesium, calcium, or strontium.

As specific compounds of alkali metal hydroxide or alkali-earth metal hydroxide, it is possible to mention lithium hydroxide, sodium hydroxide, potassium hydroxide, calcium hydroxide, magnesium hydroxide, strontium hydroxide, etc. Of these, potassium hydroxide, sodium hydroxide, calcium hydroxide, and magnesium hydroxide are preferable. Furthermore, potassium hydroxide and sodium hydroxide are particularly preferable, since they are available with low price in industrially large amount. Furthermore, as specific compounds of alkali metal alkoxide, it is possible to mention sodium methoxide, sodium ethoxide, etc.

Furthermore, it is also possible to conduct the reaction by using an alkali metal or alkali-earth metal carbonate (sodium carbonate, potassium carbonate, lithium carbonate, calcium carbonate, sodium hydrogencarbonate, potassium hydrogencarbonate, lithium hydrogencarbonate, etc.) or carboxylate (sodium acetate, potassium acetate, etc.) as an inorganic base having midrange basicity. There is small merit to particularly use is, since is also requires a further reaction time as compared with the above-mentioned base having high basicity.

Furthermore, the base used in the present invention can also be used by one kind or by a combination of at least two kinds.

The amount of the base used in the present invention is required to be at least 1 mol relative to 1 mol of (Z)-1-halogeno-3,3,3-trifluoropropene represented by formula [1]. It can suitably be selected in a range of normally 1-10 mols, preferably 1-4 mols, more preferably 1-2 mols, per 1 mol of the compound of formula [1]. Furthermore, it is also possible to use the base by more than 10 mols, but there is no merit either to use it in particularly large amount Furthermore, in the present invention, in the case of using the base in less than 1 mol relative to 1 mol of the compound of formula [1], conversion of the reaction may lower. Then, at the time of purification operation after the reaction, the unreacted (Z)-1-halogeno-3,3,3-trifluoropropene can also be recovered and recycled in the next reaction.

In the present invention, it is possible to separately add solvent. The solvent is not particularly limited as long as it is not involved in the reaction. For example, it can be exemplified by alkanes such as n-pentane, n-hexane, n-heptane, n-octane, etc., aromatic hydrocarbons such as benzene, toluene, xylene, etc., ethers such as diethyl ether, tetrahydrofuran, dioxane, etc., halogenated hydrocarbons such as dichloromethane, chloroform, etc., ketones such as acetone, methyl ethyl ketone, methyl isobutyl ketone, etc., nitriles such as acetonitrile, propionitrile, butylnitrile, etc., amides such as N,N-dimethylformamide (DMF), N,N-dimethylacetoamide (DMAC), hexamethylphosphoric triamide (HMPA), etc., glycols such as ethylene glycol, diethylene glycol, ethylene glycol monomethyl ether, ethylene glycol monoacetate, etc., alcohols such as methanol, ethanol, 2-propanol, etc., water, etc. Furthermore, these solvents can also be used by one kind or by a combination of at least two kinds.

From easiness of operability, the base used in the present invention can also be added as a solution by separately adding the above-mentioned solvent in case that the base is solid under ordinary temperature and ordinary pressure. Furthermore, concentration of the solution can suitably be adjusted by a person skilled in the art to the extent that the reaction proceeds sufficiently or to the extent that the base is sufficiently dissolved in the solvent. Although it depends on the base, for example, in the case of potassium hydroxide aqueous solution, it is adjusted normally to 5-85 mass %, preferably 20-60 mass %, more preferably a range of 25-50 mass %.

Furthermore, with respect to the base used in the present invention, it is also possible to use that with no solvent by adding no solvent (details are mentioned hereinafter) or to react that as a solution by separately adding that to at least one kind of solvent, according to the kind of inorganic base and organic base and the state (solid or liquid) under ordinary temperature and ordinary pressure. It can suitably be selected by a person skilled in the art.

For example, as shown in Examples 1-7, it is one of particularly preferable modes in the present invention to use potassium hydroxide or sodium hydroxide as the base, and water, methanol or ethanol as the solvent to (Z)-1-halogeno-3,3,3-trifluoropropene.

Furthermore, in the present invention, since (Z)-1-halogeno-3,3,3-trifluoropropene as the starting raw material is in liquid under ordinary temperature and ordinary pressure, that in itself serves as a solvent. Thus, we have obtained a finding that 3,3,3-trifluoropropyne, which is the target product, is obtained with high selectivity and high yield by conducting the reaction under a condition that the solvent is not particularly required, that is, under a condition that the solvent is not made to coexist in the reaction system. For example, in Example 7, it is one of particularly preferable modes to conduct the reaction under a condition that the solvent is not made to coexist with (Z)-1,3,3,3-tetrafluoropropene.

Furthermore, under a condition that the solvent is not made to coexist, which is mentioned here, refers to that the solvent is substantially not made to exist in the system. Specifically, it refers to the amount of 3 mass % or less, preferably 1 mass % or less, more preferably 0.1 mass % or less, relative to (Z)-1-halogeno-3,3,3-trifluoropropene. As long as the reaction is conducted by not positively adding these substances to the system, it is easy to accomplish a condition that the solvent is not made to coexist.

In the present invention, besides solvent, it is also possible to use a phase-transfer catalyst as an additive. In the case of using a phase-transfer catalyst, the reaction is accelerated in the case of using particularly an alkali metal hydroxide as the base. For this reason too, it is preferably used.

As the phase-transfer catalyst, it is possible to use a crown ether, cryptand, or onium salt. Crown ether is capable of enhancing reactivity by including a metal cation, and it is possible to mention a combination of K cation and 18-crown-6, that of Na cation and 15-crown-5, that of Li cation and 12-crown-4, etc. Furthermore, a dibenzo or dicyclohexano derivative of crown ether, and the like are also useful.

Cryptand is a polycyclic macrocyclic chelator. For example, it is capable of activating the reaction by forming a complex (cryptate) with K cation, Na cation, Cs cation or Li cation. It is possible to mention 4,7,13,18-tetraoxa-1,10-diazabicyclo[8.5.5]icosane (cryptand 211), 4,7,13,16,21,24-hexaoxa-1,10-diazabicyclo[8.8.8]hexacosane (cryptand 222), etc.

In the onium salt, there exists quaternary ammonium salt or quaternary phosphonium salt. It is possible to mention tetramethylammonium chloride, tetramethylammonium bromide, tetra-n-butylammonium chloride, tetra-n-butylammonium bromide, benzyltriethylammonium chloride, methyltrioctylammonium chloride, tetra-n-butylphosphonium chloride, tetra-n-butylphosphonium bromide, and methyltriphenylphosphonium chloride.

In the present invention, the reaction pressure is not particularly limited. It can be operated under ordinary pressure or pressurized condition, 0-2 MPa (absolute pressure standard, hereinafter it is the same), preferably 0-0.5 MPa.

The reaction temperature is not particularly limited. It is possible to select a liquid phase condition or gas phase condition as the reaction system in relation with the reaction pressure. It is 0-80° C., preferably 25° C. to 40° C. at around ordinary temperature.

Furthermore, it is particularly preferable in the present invention to conduct the reaction in liquid phase. (Z)-1-halogeno-3,3,3-trifluoropropene as the starting raw material is in liquid under ordinary temperature and ordinary pressure, but it is possible to conduct the reaction by turning the inside of the reaction system into gas phase condition and by sealing the reaction container. In the case of conducting the present reaction under gas phase condition, however, (Z)-1-halogeno-3,3,3-trifluoropropene as the starting raw material tends to turn into E form, which has almost no reactivity and is more stable, thereby lowering yield. Therefore, it is one of particularly preferable characteristics in the present invention to conduct the present reaction in liquid phase.

In the method of the present invention, no corrosive gas is generated. Therefore, material of the reactor is not particularly limited as long as it resists against pressure when conducting the reaction under ordinary pressure or pressurization. It is possible to use a reaction container made of a general stainless steel, glass or fluorine resin, or of a material lined with glass or fluorine resin.

Furthermore, it is also possible to use a pressure-proof reaction container. Even in the case of liquefied condition, the reaction proceeds without so much increase of pressure of the inside of the reaction system. Therefore, it can sufficiently be conducted even under ordinary pressure. Accordingly, there is no large merit to use particularly a pressure-proof reaction container.

Furthermore, 3,3,3-trifluoropropyne obtained by the method of the present invention exists as a gas under normal temperature and normal pressure. It is possible to obtain 3,3,3-trifluoropropyne of high purity by allowing the gas obtained after the reaction to flow through a cooled condenser, then collecting and liquefying the gas in a collecting container, and then further conducting a rectification without conducting a post-treatment.

Furthermore, in the present invention, it may be conducted by a continuous or semi-continuous or batch manner. A person skilled in the art can suitably adjust it.

In the following, the present invention is explained more in detail by examples, but it is not limited to these examples. Here, "%" of the compositional analysis value represents "area %" of a composition obtained by measuring the reaction mixture directly by gas chromatography (unless particularly mentioned, the detector is FID).

EXAMPLE 1

A 500 ml, three-necked, round bottom flask made of glass and equipped with a two-stage cooling tower formed of a glass refrigerator in which a refrigerant of −20° C. is circulated and a Dewar vessel type condenser adjusted to −40° C. and a thermocouple-introducing, glass, protecting tube was charged with 56.11 g (1.0 mol) of potassium hydroxide, 84.21 g of water and 84.21 g of methanol, followed by stirring with a magnetic stirrer with cooling for dissolution. Then, a dropping funnel containing (Z)-1-chloro-3,3,3-trifluoropropene was attached, and it was heated in a water bath to increase the inside temperature to 38° C. and maintained. When the inside temperature became stable, 130.5 g (1.0 mol) of (Z)-1-chloro-3,3,3-trifluoropropene was added dropwise by spending 2 hours. 3,3,3-trifluoropropyne gas of high concentration generated by the reaction was liquefied and collected in a collecting trap (cooled by methanol and dry ice) led at outlet of the condenser. After termination of the dropping of (Z)-1-chloro-3,3,3-trifluoropropene, the heating was further continued for 30 minutes. Then, the reactor was cooled down to terminate the reaction.

After termination of the reaction, 92.17 g of the collected liquid was obtained on the collecting trap side.

On the other hand, the residue in the flask was subjected to a two-layer separation and a flash distillation operation to collect an organic matter except the solvent used. With this, the unreacted raw material and high-boiling-point substances were obtained by 3.53 g. These collected liquids were analyzed with a gas chromatograph. With this, conversion of (Z)-1-chloro-3,3,3-trifluoropropene was 98.6%, selectivity of 3,3,3-trifluoropropyne was 98.3%, and yield of 3,3,3-trifluoropropyne was 96.9%.

EXAMPLE 2

The experiment was conducted in the same manner as that of Example 1, except in that 130.5 g (1.0 mol) of (Z)-1-chloro-3,3,3-trifluoropropene was used, and 61.7 g (1.1 mols) of potassium hydroxide, 92.6 g of water and 92.6 g of methanol were used. As a result, 92.6 g of the collected liquid was obtained on the collecting trap side, and 2.9 g of an organic matter except the solvent used, which had been collected from the residue in the flask, was obtained. These collected liquids were analyzed with a gas chromatograph. With this, conversion of (Z)-1-chloro-3,3,3-trifluoropropene was 99.2%, selectivity of 3,3,3-trifluoropropyne was 98.4%, and yield of 3,3,3-trifluoropropyne was 97.6%.

EXAMPLE 3

The experiment was conducted in the same manner as that of Example 1, except in that 130.5 g (1.0 mol) of (Z)-1-chloro-3,3,3-trifluoropropene was used, and 61.7 g (1.1 mols) of potassium hydroxide, 92.6 g of water and 92.6 g of ethanol were used. As a result, 86.0 g of the collected liquid was obtained on the collecting trap side, and 15.5 g of an organic matter except the solvent used, which had been collected from the residue in the flask, was obtained. These collected liquids were analyzed with a gas chromatograph. With this, conversion of (Z)-1-chloro-3,3,3-trifluoropropene was 96.4%, selectivity of 3,3,3-trifluoropropyne was 94.0%, and yield of 3,3,3-trifluoropropyne was 90.6%.

EXAMPLE 4

The experiment was conducted in the same manner as that of Example 1, except in that 130.5 g (1.0 mol) of (Z)-1-chloro-3,3,3-trifluoropropene was used, and 44.00 g (1.1 mols) of sodium hydroxide, 66.00 g of water and 66.00 g of methanol were used. As a result, 79.2 g of the collected liquid was obtained on the collecting trap side, and 25.7 g of an organic matter except the solvent used, which had been collected from the residue in the flask, was obtained. These collected liquids were analyzed with a gas chromatograph. With this, conversion of (Z)-1-chloro-3,3,3-trifluoropropene was 95.6%, selectivity of 3,3,3-trifluoropropyne was 87.7%, and yield of 3,3,3-trifluoropropyne was 83.8%.

EXAMPLE 5

The experiment was conducted in the same manner as that of Example 1, except in that 130.5 g (1.0 mol) of (Z)-1-chloro-3,3,3-trifluoropropene was used, and 67.34 g (1.2 mols) of potassium hydroxide, 157.13 g of water and 1.6 g (5.9 mmol) of crown ether (18-crown-6) were used, and methanol was not added. As a result, 4.0 g of the collected liquid was obtained on the collecting trap side, and 124.8 g of an organic matter except the solvent used, which had been collected from the residue, was obtained. These collected liquids were analyzed with a gas chromatograph. With this, conversion of (Z)-1-chloro-3,3,3-trifluoropropene was 75.0%, selectivity of 3,3,3-trifluoropropyne was 88.0%, and yield of 3,3,3-trifluoropropyne was 66.0%.

EXAMPLE 6

The experiment was conducted in the same manner as that of Example 1, except in that 114.0 g (1.0 mol) of (Z)-1,3,3,3-tetrafluoropropene was used. As a result, 51.7 g of the collected liquid was obtained on the collecting trap side, and 62.2 g of an organic matter except the solvent used, which had been collected from the residue, was obtained. These collected liquids were analyzed with a gas chromatograph. With this, conversion of (Z)-1,3,3,3-tetrafluoropropene was 54.0%, selectivity of 3,3,3-trifluoropropyne was 84.0%, and yield of 3,3,3-trifluoropropyne was 45.4%.

EXAMPLE 7

A 500 ml volume, SUS-316 reactor equipped with a pressure gauge and an ejecting valve was charged with 16.80 g (0.3mols) of ground potassium hydroxide and 26.10 g (0.2mols) of (Z)-1,3,3,3-tetrafluoropropene. After sealing, it was heated at 70° C. for 9 hours while stirring it with a magnetic stirrer. The final pressure at that time was 0.5 MPa. After termination of the reaction, the ejecting valve was opened, and the organic matter was liquefied and collected in a collecting trap (cooled by methanol and dry ice). The collected organic matter was in 21.44 g. These collected liquids were analyzed with a gas chromatograph. With this, conversion of (Z)-1,3,3,3-tetrafluoropropene was 64.5%, selectivity of 3,3,3- trifluoropropyne was 98.4%, and yield of 3,3,3-trifluoropropyne was 63.5%.

REFERENCE EXAMPLE 1

The experiment was conducted in the same manner as that of Example 1, except in that 130.5 g (1.0 mol) of (E)-1-chloro-3,3,3-trifluoropropene was used, and 56.11 g (1.0 mol) of potassium hydroxide, 84.21 g of water, and 84.21 g of methanol were used, and the reaction temperature was set at 25° C. As a result, 130.50 g of an organic matter except the solvent used, which had been collected from the residue, was obtained, but the collected liquid on the collecting trap side was in 0 g. These collected liquids were analyzed with a gas chromatograph. With this, (E)-1-chloro-3,3,3-trifluoropropene did not react at all, and the production of 3,3,3-trifluoropropyne was not found.

Thus, it is understood from the results of Examples 1-7 and Reference Example 1 that, in the case of using (E/Z)-1-chloro-3,3,3-trifluoropropene, it is possible to allow the reaction to proceed better and to obtain the target product with higher selectivity by using the cis form (Z configuration), but the reaction does not proceed at all in the case of the trans form (E configuration).

The invention claimed is:

1. A method for producing 3,3,3-trifluoropropyne, comprising reacting a base with (Z)-1-halogeno-3,3,3-trifluoropropene represented by formula [1],

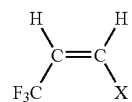

[1]

wherein X represents a fluorine or chlorine.

2. A method according to claim 1, wherein the base is at least one inorganic base selected from the group consisting of ammonia, alkali metal alkoxides, alkali metal carbonates, alkali-earth metal carbonates, alkali metal hydroxides, and alkali-earth metal hydroxides.

3. A method according to claim 2, wherein the alkali metal is lithium, sodium, potassium, rubidium, or cesium, and the alkali-earth metal is magnesium, calcium, or strontium.

4. A method according to claim 1, wherein the base is sodium hydroxide or potassium hydroxide.

5. A method according to claim 1, wherein, when the base is reacted with the (Z)-1-halogeno-3,3,3-trifluoropropene, the reaction is conducted by adding a phase-transfer catalyst into a system of the reaction.

6. A method according to claim 5, wherein the phase-transfer catalyst is a crown ether, cryptand, or onium salt.

7. A method according to claim 1, wherein the reaction is conducted in liquid phase.

* * * * *